:

US007483152B2

(12) United States Patent
Jovancicevic et al.

(10) Patent No.: US 7,483,152 B2
(45) Date of Patent: Jan. 27, 2009

(54) HIGH RESOLUTION STATISTICAL ANALYSIS OF LOCALIZED CORROSION BY DIRECT MEASUREMENT

(75) Inventors: Vladimir Jovancicevic, Richmond, TX (US); Samuel Everett Campbell, Richmond, TX (US)

(73) Assignee: Baker Hughes Incorporated, Houston, TX (US)

( * ) Notice: Subject to any disclaimer, the term of this patent is extended or adjusted under 35 U.S.C. 154(b) by 383 days.

(21) Appl. No.: 11/063,363

(22) Filed: Feb. 23, 2005

(65) Prior Publication Data

US 2005/0213430 A1      Sep. 29, 2005

Related U.S. Application Data

(60) Provisional application No. 60/549,826, filed on Mar. 3, 2004.

(51) Int. Cl.
*G01B 11/14* (2006.01)
(52) U.S. Cl. ...................................................... 356/614
(58) Field of Classification Search ................. 356/390, 356/392, 398, 614, 625, 600; 73/86; 324/700
See application file for complete search history.

(56) References Cited

U.S. PATENT DOCUMENTS

| 4,260,259 | A |   | 4/1981  | Kirk |
|-----------|---|---|---------|------|
| 4,597,294 | A | * | 7/1986  | Brill et al. ..................... 73/623 |
| 4,893,286 | A |   | 1/1990  | Cobb |
| 4,953,147 | A |   | 8/1990  | Cobb |
| 5,208,162 | A | * | 5/1993  | Osborne et al. ................. 436/6 |
| 5,376,331 | A | * | 12/1994 | Bucher et al. ................. 422/18 |
| 5,594,548 | A | * | 1/1997  | Kobayashi et al. ........... 356/602 |
| 5,671,050 | A | * | 9/1997  | de Groot ...................... 356/497 |
| 6,392,749 | B1 | * | 5/2002 | Meeks et al. ................. 356/634 |
| 6,792,357 | B2 | * | 9/2004 | Menon et al. ................. 702/27 |
| 7,040,390 | B2 | * | 5/2006 | Tubel et al. ................... 166/64 |
| 7,084,979 | B1 | * | 8/2006 | Aiyer .......................... 356/369 |
| 2002/0148560 | A1 | * | 10/2002 | Carr ....................... 156/345.24 |

FOREIGN PATENT DOCUMENTS

DE      4139107 C1     7/1993
WO   WO 2004/074808 A2   9/2004

OTHER PUBLICATIONS

N. G. H. Meyerdorf, et al., "Nondestructive Materials Characterization," 2004, pp. 37-46, Springer, Germany.

M. Koul, et al., "Topographical Analysis of Corrosion Damage in AA7075-T6 using Laser Profilometry," 6th Joint FAA/DoD/NASA Conference on Aging Aircraft, San Francisco, CA, Sep. 16-19, 2002; available at http://www.galaxyscientific.com/agingaircraft2002/SESSIONS/POSTERS/KOUL_PRT_PPT.pdf.
R. Leard et al., "Evaluation of CPC Effectiveness," 6th Joint FAA/DoD/NASA Conference on Aging Aircraft, San Francisco, CA, Sep. 16-19, 2002.
T. M. Linjewile, et al., "Prediction and Real-time Monitoring Techniques for Corrosion Characteristics in Furnaces," Materials at High Temperatures, in press as of Feb. 4, 2004; available at http://www.reaction-eng.com/downloads/corrosion_woburn.pdf.
P. Zhdan, "AFM Study of Pitting Corrosion Initiation in Stainless Steel," University of Surrey, Feb. 15, 1997; available Feb. 5, 2004 at http://www.surrey.ac.uk/MME/Research/SPM/8-1.html.
"Metal Corrosion Study with in-situ and ex-situ AFM," available Feb. 5, 2004 at http://sibener-group.uchicago.edu/afm/afm2.html.
C. S. Vikram, "Holography of Erosion, Corrosion, and Mechanical Wear: Possible Role of Phase-Shifting Interferometry", Optical Engineering, Soc. of Photo-optical Instrumentation Engineers, Communications, Jun. 1, 1996, pp. 1795-1796, vol. 35, No. 6.
M. Jakobi, et al., "Erosionmessung an rauhen Oberflachen mittels Streifenkontrast in der Speckle-Interferometrie", Technisches Messen, Apr. 1999, pp. 163-167, vol. 66, No. 4.
Patent Abstracts of Japan 2003050196 of Application No. 2001237375, "Method for Evaluating Grain Boundary Corrosion Sensitivity", vol. 2003, No. 6, Feb. 23, 2003.
PCT International Search Report for International Application No. PCT/US2005/006767, Jun. 27, 2005.

* cited by examiner

*Primary Examiner*—Tarifur R. Chowdhury
*Assistant Examiner*—Isiaka O Akanbi
(74) *Attorney, Agent, or Firm*—Madan, Mossman & Sriram PC

(57) ABSTRACT

The process involves first taking height measurements of a surface area at a relatively high resolution, such as 0.1 microns over a range of about 100 microns, of a particular surface area of a substrate prior to any corrosive effect on the substrate. This measurement or scan gives a first digital surface map. The substrate is then subjected to a corrosive environment. The same surface area is then measured with the same height resolution to give a second map, where the height of the surface area may be diminished or reduced in local areas or pits characteristic of localized corrosion. The two surface maps are subtracted to give a measurement of the extent of localized corrosion. The two surface maps may be subtracted electronically or digitally. This method may be accomplished over a relatively short time period, e.g. hours, as compared with conventional corrosion evaluation techniques.

17 Claims, No Drawings

HIGH RESOLUTION STATISTICAL ANALYSIS OF LOCALIZED CORROSION BY DIRECT MEASUREMENT

CROSS-REFERENCE TO RELATED APPLICATION

This application claims the benefit of U.S. provisional application No. 60/549,826 filed Mar. 3, 2004.

FIELD OF THE INVENTION

The invention relates to methods and techniques for evaluating localized corrosion of a substrate, and most particularly relates, in one non-limiting embodiment, to methods and systems for evaluating localized corrosion of a substrate in relatively short periods of time.

BACKGROUND OF THE INVENTION

Localized corrosion of equipment is a serious problem in many industries and processes. In particular, corrosion failures in many oil and gas production systems, oil/gas/water transmission pipelines, petrochemical and chemical processing plants, fossil fuel and nuclear power plants are in the form of localized corrosion which may result in loss of production, increase in maintenance cost, environmental pollution and potential health and safety hazards, etc. It is important that the occurrence of localized corrosion is identified and the severity determined in advance of structural failure due to corrosion, particularly catastrophic failure. In addition, the ability of chemicals to inhibit localized corrosion needs to be determined so that they may be effectively implemented in advance of potential corrosive problems.

The problems resulting from localized corrosion have been dealt with for many years with variable success. Localized corrosion is highly stochastic in nature and its occurrence is fairly unpredictable. Thus, it is important that statistical analysis is carried out when studying or monitoring for localized corrosion. Currently, localized corrosion is studied or monitored by measuring directly relatively large features (e.g. pits) on the surface by using standard optical microscopy with limited spatial resolution. Indirect methods are also used, such as electrochemical noise, to characterize localized (e.g. localization index) corrosion.

Further, conventional corrosion evaluation techniques typically require that the testing time extend over weeks or months so that meaningful projections or predictions about corrosion over the course of years may be developed. However, such techniques make it impossible to quickly address new environments and/or materials and develop protocols to address potential corrosion problems. It would thus be desirable of corrosion evaluation methods could be devised to shorten the testing time, yet maintain or increase the accuracy of the results.

SUMMARY OF THE INVENTION

An object of the invention is to provide a way of measuring localized corrosion of a large surface area of a substrate, such as a metal substrate.

Another object of the invention is to provide a method of statistically analyzing localized corrosion directly by measuring localized corrosion over a relatively large area.

Another object of the invention is to provide a method of determining localized corrosion rates (e.g. pit depth) that is relatively rapid, on the order of hours and days, rather than weeks and months, in one non-limiting embodiment.

In carrying out these and other objects of the invention, there is provided, in one non-limiting form, a method of analyzing localized corrosion of a substrate that involves taking height measurements of an initial surface area (in one non-limiting embodiment within 1 micron lateral resolution) of a substrate within a height resolution of at least 0.1 micron to produce an initial digital surface map. The substrate is then subjected to a corrosive environment for a time period. Height measurements of the same surface area of the substrate are then taken with same lateral and height resolution to produce a subsequent digital surface map. The two surface maps are subtracted to give a measurement of extent of localized corrosion of the surface area.

In one non-limiting embodiment of the invention, the height resolution is 0.01 microns over a range of at least 100 microns. The height measurements may be performed by techniques such as light interferometry (including white light interferometry), stylus profilometry, optical profilometry, scanning confocal microscopy, and possibly combinations thereof.

In another non-restrictive version of the invention there is provided a system for measuring and analyzing localized corrosion of a substrate that includes measuring apparatus adapted to take height measurements of a surface area of a substrate within a height resolution to produce a digital surface map. The measuring apparatus may be a light interferometer, a stylus profilometer, an optical profilometer and/or a scanning confocal microscope. The system also includes a computer for subtracting an initial digital surface map from a subsequent digital surface map of the same surface area to give a measurement of extent of localized corrosion of the surface area.

Traditionally, topographies and surface roughness are measured by moving a diamond tip in contact with the sample over its surface. Those tactile profilers show certain limitations, including, but not necessarily limited to, the destruction of soft surfaces, slow measurements and critical calibration routines. Many line scans have to be performed in order to acquire topographical data. It has been found that line scanning optical profilers or white light interferometers allow measurement of topographies of a surface to be performed quickly. One technique is based on scanning white-light interferometry, a traditional technique in which a pattern of bright and dark lines (fringes) result from an optical path difference between a reference and a sample beam. After reflection, the beams recombine inside the interferometer, undergoing constructive and destructive interference and producing the light and dark fringe pattern. A precision vertical scanning transducer and camera together generate a three-dimensional interferogram of the surface, processed by the computer and transformed by frequency domain analysis resulting in a quantitative 3-D image.

DETAILED DESCRIPTION OF THE INVENTION

A new method of measuring localized corrosion has been discovered that involves using a high resolution imaging technique (in one non-limiting instance white light interferometry and interferometer) to digitally map the small features (in another non-restrictive example, at least about 0.1 micron in z-axis, and in one non-limiting embodiment, at least about 0.01) resulting from localized corrosion superposed on an original surface (in another non-restrictive example, less than 10 micron in z-axis). Such method works well to evaluate corrosion of an intrinsically rough, metal surface. This is accomplished by subtracting one data set obtained before corrosion from the data set obtained after the surface exposure to a corrosive environment. The new technique should permit reduction of time required to generate measurable localized corrosion rate in the lab (i.e. pits) to be achieved (in a non-restrictive case, in hours or days instead of weeks or months). Samples or coupons or substrates of a material identical or substantially the same as the being protected may be used, or optionally the substrate may be the actual object being protected. That is, it is expected that in most cases the samples, coupons or substrates are representative of the system, whereas it may be impractical or impossible to take measurements of part of the system per se, such as a downhole tool or tubular good.

Further, the present invention relates to the detection and direct measurement of localized corrosion (that may or may not be in the form of pitting) in a quantitative and statistically evaluated manner. The depth and spatial distribution of the localized events are determined by direct measurement using high height-resolution techniques (in one non-limiting embodiment, at least 0.01 micron in the z-axis direction or height) with a large range (at least 100 microns in the z-axis direction) and lateral area (at least 0.05 cm$^2$) including, but not necessarily limited to, white light interferometry, optical profilometry, and stylus profilometry. Laser profilometry is not anticipated to be useful for these measurements because it does not provide sufficient spatial and depth resolution for examining localized corrosion events.

The precise quantification of localized events, which are typically of the order of 0.1 to 1 micron in depth, is made by performing the measurement both before and after exposure to a corrosive environment for a period of hours, days or weeks. The samples must be spatially aligned with high precision (0.5 micron) during both measurements. The height difference or metal loss for the entire sample is determined by image subtraction, for instance electronic subtraction of two digital images. Localized corrosion effects which are unacceptable in long life equipment (for instance, many years) and could not be measured using standard methodology may be measured using a short duration laboratory test (on the order of hours, e.g.) of the methods herein. In addition, by measuring over a relatively large surface area, a statistically significant number of localized events may be measured in one experiment providing spatial and depth (penetration) rate measurements. Average and maximum pitting rates may also be determined using a rapid analysis technique on short duration experiments. The same techniques may also be applied to operational equipment and field coupons allowing for a quicker measurement response which typically takes 3 to greater than 6 months exposure prior to measurement.

The best method to quantify localized corrosion is by direct measurement of the size and depth of each individual event (pit). While localized attack may be inferred from noise measurements, it is not a measurement of the absolute or maximum depth of any pit or the distribution of events. The maximum depth and pit size can be measured by optical microscopy but the depth resolution is limited to about 5 microns. Tests using optical microscopy as the measurement method must be run for a significant time period to achieve measurable localized corrosion (weeks or months), and even then, short-term localized corrosion events which correspond to unacceptable penetration rates may be missed. AFM (atomic force microscopy) and STM (scanning tunneling microscopy) may be used to look at localized corrosion of very small depths but may not necessarily be effectively used on surfaces that have a large intrinsic roughness or over large surface areas. It is expected that the methods and systems described herein will be useful on surfaces that have a large intrinsic roughness or over relatively large surface areas.

An initial high resolution measurement of the surface profile of any coupon or substrate sample is collected. The measurement or surface image is taken over a relatively large area and the area may be increased by "stitching" images together electronically using appropriate software. Stitching images together increases the range and therefore the accuracy and reliability of the results. In the measurement, the height resolution is submicron and the lateral resolution is similar to that achieved using an optical microscope. Measuring the height of each surface area and piecing them together may be repeated until the whole or entire surface area is stitched and mapped. The surface profile is stored electronically as a digital image with height data along with spatial data. As noted, the instruments suitable for use include, but are not necessarily limited to, a white light interferometer, a stylus profilometer, or an optical profilometer.

The coupon or substrate is placed in an environment where localized corrosion occurs for the desired duration, depending on the particular metallurgy, whether or not a corrosion inhibitor is used, and the strength of the corrosive agents in the environment. It is expected that the corrosive environment contains one or more corrosive agents, including, but not necessarily limited to, organic and inorganic acids, organic and inorganic bases, acid gases such as hydrogen sulfide and carbon dioxide, organic or inorganic scales, and oxygen. These corrosive environments may or may not have other factors present as well, including, but not necessarily limited to, electrical fields and magnetic fields, high or low temperatures, high and low pressures, mechanical action or abrasion, flowing fluids etc. After controlled exposure, the coupon is removed from the corrosive environment and protected from additional corrosion.

The corroded surface area is precisely located again in the instrument such that the same surface area is imaged in the same orientation within the resolution of the instrument (e.g. 0.5 micron). The surface area is re-imaged completely to give a subsequent or possibly final surface map. By subtracting the initial and subsequent surface maps, the precise change in depth or metal loss or corrosion rate (change in depth over time) may be stated for any point on the surface. It is expected that in some cases it may be desirable to image a series of surface maps over time, subtracting each in sequence or over a regular periodic time interval. It is expected that in most embodiments of the invention, the surface maps will be digital and the subtraction will be performed by a computer electronically. The depths may then be characterized in size and rate distribution by statistical analysis. This will allow measurement of penetration rate at any point as opposed to an average general corrosion rate. The maximum penetration rate at the point with the largest change should be more indicative of metal lifetime. In addition, the method provides an improved method by which to evaluate corrosion inhibitor performance based upon actual inhibition of localized corrosion. In another non-restrictive alternative, the evaluative methods herein do not employ polygonal modeling.

The statistical methods (e.g. standard deviation, regression analysis) rely on large sample pits size to determine the pit depth distribution, average pit depth and largest pit depth. It can also allow prediction of pit growth over time to be estimated.

Further, although it is contemplated that the method of this invention is expected to be used on metal substrates, such as to determine the extent of corrosion of iron, iron-alloys such as various steel alloys and other alloys, it is contemplated that the inventive method could be easily adapted to measure corrosion of other metals and materials. Additionally, it may be understood that the techniques and methods of this invention could also be used to study, evaluate and analyze other processes beside corrosion that are stochastic in nature requiring statistical measurement of numerous events and high resolution detection. Processes of eating away or diminishing a material besides corrosion that could be studied with the inventive method include, but are not necessarily limited to, erosion, attrition, etching, nanomanufacture, sublimation, etc.

In one non-limiting embodiment of the invention, the height resolution of the method is at least 0.01 microns (z-axis) over a range of at least 100 microns. In another non-limiting embodiment, the height resolution is at least 0.01 microns (z-axis) over a range of at least 100 microns.

It should be understood that the invention herein may be part of a larger process, such as an evaluative method of a particular substrate for at least one particular corrosion characteristic. Examples of such larger processes or methods may include, but are not necessarily limited to, evaluating a new metal alloy in a variety of possibly corrosive environments where it may be used, or evaluating a particular corrosive agent or combination of agents. On the other hand, the inventive process could be used to evaluate one or more chemical corrosion inhibitors or other corrosion inhibiting methods using a particular substrate and/or particular set of corrosive conditions or environments to determine their ability to control localized corrosion.

Further, it is also expected or anticipated that the method of this invention could be used as part of a process for inhibiting corrosion of a particular substrate in a certain industrial or technological environment. For instance, the method of this invention could be part of a continuous corrosion monitoring method for hydrocarbon production or refining processes, nuclear power plants, or semiconductor manufacturing procedures.

This invention provides a commercial and technical advantage over other methods by offering a technique which can quantitatively assess localized corrosion rates directly and statistically using short term testing. The method will also allow for an improved technique of ranking materials and/or corrosion inhibitors for their ability to control localized corrosion which is known to be the main failure mechanism in field applications. Indeed, the system for implementing the methods described herein may include a mechanism for introducing a corrosion inhibitor to the substrate including, but not necessary limited to, an injection system for introducing a corrosion inhibitor to the substrate at regular time intervals, an injection system for introducing a corrosion inhibitor to the substrate on a basis as needed as determined by the system that periodically measures the substrate corrosion, and the like.

Many modifications may be made in the methods of and implementation of this invention without departing from the spirit and scope thereof that are defined only in the appended claims. For example, the exact corrosion characteristics measured may be different from those used explicitly mentioned or suggested here. Additionally, techniques and methods for directly measuring distances at high resolution other than those specifically mentioned may find utility in the methods of this invention. Various combinations of substrates, corrosive environments, corrosion inhibitors, corrosion inhibiting techniques and measurement processes besides those explicitly mentioned herein are expected to be useful.

We claim:

1. A method of measuring and analyzing localized corrosion of a substrate comprising:

locating a substrate in an orientation in a measuring apparatus;

taking height and spatial measurements of an initial surface area of the substrate within a height and spatial resolution to produce an initial digital surface map;

subjecting the substrate to a corrosive environment for a time period;

locating the substrate in the measuring apparatus in the same orientation;

taking height and spatial measurements of the same surface area of the substrate within the height and spatial resolution to produce a subsequent digital surface map;

subtracting the subsequent digital surface map from the initial digital surface map to give a measurement of extent of localized corrosion of the surface area; and statistically analyzing the measurement of extent of localized corrosion to determine a characteristic selected from the group consisting of corrosion depth (penetration) rate, spatial pit distribution, average pitting rate, maximum pitting rate, and combinations thereof, in the absence of laser profilometry.

2. The method of claim 1 where the measuring apparatus taking the height and spatial measurements performs a technique selected from the group consisting of white light interferometry, stylus profilometry, optical profilometry, scanning confocal microscopy and combinations thereof.

3. The method of claim 1 where the height and spatial resolution is at least 0.1 microns over a range of at least 100 microns.

4. The method of claim 1 where the method is repeated for at least an adjacent surface area, and the initial digital surface maps of the two surface areas are stitched together.

5. The method of claim 4 where the method is repeated and surface maps are stitched together until an entire substrate surface is mapped.

6. The method of claim 1 where the surface maps are subtracted digitally.

7. The method of claim 1 where the time period ranges from about 1 hour to about 1 week.

8. The method of claim 1 where the initial surface area is at least 0.05 cm$^2$.

9. The method of claim 1 where the method further comprises an evaluation of a substrate material for at least one corrosion characteristic.

10. The method of claim 1 where the method further comprises an evaluation of a corrosion inhibitor.

11. The method of claim 1 where the method further comprises employing at least one process for inhibiting corrosion of the substrate.

12. A method of analyzing localized corrosion in a system comprising:

locating a system or a substrate representative of the system in an orientation in a measuring apparatus;

taking height and spatial measurements of an initial surface area of the system or the substrate within a height and spatial resolution to produce an initial digital surface map, where the height and spatial resolution is at least 0.1 microns over a range of at least 100 microns;

subjecting the substrate to a corrosive condition for a time period;

locating the substrate in the measuring apparatus in the same orientation;

taking height and spatial measurements of the same surface area of the substrate within the height and spatial resolution to produce a subsequent digital surface map;

subtracting the subsequent digital surface map from the initial digital surface map to give a measurement of extent of localized corrosion of the initial surface area;

statistically analyzing the measurement of extent of localized corrosion to determine a characteristic selected from the group consisting of corrosion depth (penetration) rate, spatial pit distribution, average pitting rate, maximum pitting rate, and combinations thereof, where the measuring apparatus taking the height and spatial measurements performs a technique selected from the group consisting of white light interferometry, stylus profilometry, optical profilometry, scanning confocal microscopy and combinations thereof, in the absence of laser profilometry.

13. The method of claim 12 where the method is repeated for at least an adjacent surface area, and the initial surface maps of the two surface areas are stitched together.

14. The method of claim 13 where the method is repeated and surface maps are stitched together until an entire substrate surface is mapped.

15. The method of claim 12 where the surface maps are subtracted digitally.

16. The method of claim 12 where the time period ranges from about 1 hour to about 1 week.

17. The method of claim 12 where the surface area is at least $0.05$ cm$^2$.

* * * * *